United States Patent
Jacquot

(10) Patent No.: US 6,818,796 B2
(45) Date of Patent: Nov. 16, 2004

(54) METHOD FOR PREPARING FLUORINATED KETONES

(75) Inventor: Roland Jacquot, Francheville (FR)

(73) Assignee: Rhodia Chimie, Cedex (FR)

(*) Notice: Subject to any disclaimer, the term of this patent is extended or adjusted under 35 U.S.C. 154(b) by 0 days.

(21) Appl. No.: 10/415,806

(22) PCT Filed: Oct. 26, 2001

(86) PCT No.: PCT/FR01/03337

§ 371 (c)(1), (2), (4) Date: Sep. 26, 2003

(87) PCT Pub. No.: WO02/36536

PCT Pub. Date: May 10, 2002

(65) Prior Publication Data

US 2004/0054234 A1 Mar. 18, 2004

(30) Foreign Application Priority Data

Nov. 6, 2000 (FR) .............................. 00 14176

(51) Int. Cl.⁷ .............................................. C07C 45/00
(52) U.S. Cl. ...................... 568/319; 568/346; 568/397; 568/398
(58) Field of Search ................................ 568/319, 346, 568/397, 398

(56) References Cited

U.S. PATENT DOCUMENTS 4,172,851 A * 10/1979 Childs

FOREIGN PATENT DOCUMENTS

| EP | 085996 | * | 8/1983 |
| EP | 283660 | * | 9/1988 |
| EP | 352674 | * | 1/1990 |

* cited by examiner

Primary Examiner—Paul J. Killos

(57) ABSTRACT

A subject of the present invention is a process for preparation of fluorinated ketones corresponding to general formula (I) $R_1$—CO—$R_2$ in which $R_1$ and $R_2$ are as defined in claim 1, characterized in that it consists of reacting two carboxylic acids of Formula (II), $R_1$—COOH and Formula (III), $R_2$—COOH, in the gaseous phase and in the presence of a catalyst comprising at least one oxide of an element chosen from the rare earths, thorium, titanium and aluminum.

36 Claims, No Drawings

METHOD FOR PREPARING FLUORINATED KETONES

This application is an application under 35 U.S.C. Section 371 of International Application Number PCT/FR01/103337 filed on Oct. 26, 2001.

A subject of the present invention is a process for preparation of fluorinated ketones. The invention is used more particularly for ketones having at least one fluorine atom, preferably three fluorine atoms at position α with respect to the carbonyl group.

It is known to prepare an α-trifluorinated ketone which consists of reacting an organometallic compound with trifluoroacetic acid or its esters [Chem. L. S. et al, J. Fluorine Chem. VIII, p. 117 (1981)].

This process has several disadvantages. It includes several stages, preparation of the organometallic compound from bromobenzene, then reaction with trifluoroacetic acid at a low temperature (−78° C.) and hydrolysis, which complicates its implementation, and it is difficult to transfer to an industrial scale. Moreover, the reaction yield is not satisfactory due to the formation of by-products.

It is also known, in a general fashion, to prepare a ketone from one or more carboxylic acids according to the Piria reaction which consists of reacting the carboxylic acid or acids in the gaseous phase, in the presence of a metal oxide which can be chosen from the alkaline, alkaline-earth metal oxides, oxides of the metals of the groups IIIb, IVb and Vb.

It turns out that the preparation of a fluorinated ketone and more particularly an α-trifluorinated ketone according to the Piria reaction has not been described in the literature, as defluorination of the starting reagent is carried out at high temperature, thus leading to fluorination of the catalyst.

A process has now been found, which constitutes the subject of the present invention, for preparation of a fluorinated ketone corresponding to the general formula:

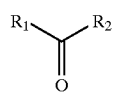
(I)

in which:
R$_1$ and R$_2$, which are identical or different, represent a hydrocarbon group containing 1 to 40 carbon atoms, which can be a linear or branched, saturated or unsaturated acyclic aliphatic group; a monocyclic or polycyclic, saturated, unsaturated or aromatic carbocyclic or heterocyclic group; a sequence of the above-mentioned groups.

at least one of the R$_1$ and R$_2$ groups does not comprise hydrogen atoms on the carbon atom at position α with respect to the carbonyl group, at least one of the R$_1$ and R$_2$ groups comprises one or more fluorine atoms, said process being characterized in that, in the gaseous phase, a carboxylic acid of Formula (II):

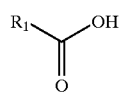
(II)

in which R$_1$ is as defined above, and a carboxylic acid of formula (III):

(III)

in which R$_2$ is as defined above,
is reacted in the presence of a catalyst comprising at least one oxide of an element chosen from the rare earths, thorium, titanium and aluminum.

By "rare earth" is meant the lanthanides having an atomic number from 57 to 71, and yttrium as well as scandium.

According to the invention, carboxylic acids of Formulae (II) and (III) are divided, but the invention includes the use of carboxylic acid derivatives such as carboxylic acid anhydrides or corresponding ketenes.

The invention makes it possible to obtain symmetrical ketones if, in Formula (I), R$_1$ is identical to R$_2$, and asymmetrical ketones if R$_1$ is different from R$_2$.

More precisely, in Formulae (I) to (III), R$_1$ and R$_2$ represent a hydrocarbon group having 1 to 20 carbon atoms, which can be a linear or branched, saturated or unsaturated acyclic aliphatic group; a monocyclic or polycyclic, saturated, unsaturated or aromatic, carbocyclic or heterocyclic group; a linear or branched, saturated or unsaturated aliphatic group, carrying a cyclic substituent.

R$_1$ and R$_2$ preferably represent a linear or branched, saturated acyclic aliphatic group, preferably having 1 to 12 carbon atoms, and yet more preferably 1 to 4 carbon atoms.

The invention does not exclude the presence of an insaturation on the hydrocarbon chain, such as one or more double bonds which can be conjugated or non-conjugated, or a triple bond.

The hydrocarbon chain can optionally be interrupted by a heteroatom (for example oxygen or sulphur) or by a functional group to the extent that the latter does not react and a group such as in particular —CO— can in particular be mentioned.

The hydrocarbon chain can optionally carry one or more substituents (for example halogen, ester) to the extent that they do not interfere with the ketonization reaction.

The linear or branched, saturated or unsaturated acyclic aliphatic group can optionally carry a cyclic substituent. By ring is meant a saturated, unsaturated or aromatic, carbocyclic or heterocyclic ring.

The acyclic aliphatic group can be bonded to the ring by a valency bond, a heteroatom or a functional group such an oxy, carbonyl, carboxy, sulfonyl group, etc.

As examples of cyclic substituents, aromatic or heterocyclic, cycloaliphatic substituents can be envisaged, in particular cycloaliphatics comprising 6 carbon atoms in the ring, or benzenic, these cyclic substituents themselves optionally carrying any substituent to the extent that they do not impede the reactions intervening in the process of the invention. The alkyl, alkoxy groups having 1 to 4 carbon atoms can be mentioned in particular.

Among the aliphatic groups carrying a cyclic substituent, reference is made more particularly to the cycloalkylalkyl groups, for example cyclohexylalkyl, or the aralkyl groups having 7 to 12 carbon atoms, in particular benzyl or phenylethyl.

In Formulae (I) to (III), R$_1$ and R$_2$ can also represent a saturated or unsaturated carbocyclic group preferably having 5 or 6 carbon atoms in the ring; a saturated or unsaturated heterocyclic group, containing in particular 5 or 6 carbon atoms in the ring, including 1 or 2 heteroatoms such as nitrogen, sulphur and oxygen atoms; a monocyclic, aromatic carbocyclic or heterocyclic group, preferably phenyl, pyridyl, pyrazolyl, imidazolyl or polycyclic, condensed or non-condensed, preferably naphthyl.

As soon as one of the $R_1$ and $R_2$ groups comprises a ring, this can also be substituted. The substituent can be of any kind, to the extent that it does not interfere with the principal reaction. The number of substituents is generally 4 per ring at the most, but most often equal to 1 or 2.

Among all the meanings previously given for $R_1$ and $R_2$, they preferably represent a linear or branched alkyl group having 1 to 12 carbon atoms, preferably 1 to 6 carbon atoms or a phenyl group.

As previously mentioned, at least one of the $R_1$ and $R_2$ groups does not comprise hydrogen atoms on the carbon atom at position a with respect to the carbonyl group.

Therefore, one of the carbon atoms at position a with respect to the carbonyl group is a tertiary carbon atom. It can be represented by the formula $(R_3)(R_4)(R_5)C$—in which $R_3, R_4, R_5$ in particular represent a halogen atom, preferably a fluorine atom; a linear or branched alkyl group having 1 to 6 carbon atoms, the $R_3, R_4, R_5$ groups can also form a ring, for example a phenyl group.

As examples of carboxylic acids comprising a tertiary carbon atom, perfluorinated carboxylic acids can be mentioned.

In effect, the invention is used quite particularly for the preparation of fluorinated ketones from carboxylic acids, one of which is at least a fluorinated aliphatic carboxylic acid corresponding more particularly to Formula (IIa):

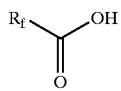

(IIa)

in which:

$R_f$ represents a perfluorinated chain of formula:

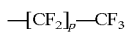

in said formula, p represents a number from 0 to 10.

The preferred aliphatic carboxylic acids correspond to Formula (IIa) in which $R_f$ preferably represents the groups:

—$CF_3$

—$CF_2$—$CF_3$

The invention is also used for the preparation of fluorinated ketones from fluorinated aromatic carboxylic acids, corresponding more particularly to Formula (IIb):

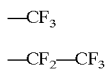

(IIb)

in which $R_f$ has the meaning given previously but preferably represents a trifluoromethyl group.

As examples of carboxylic acids of Formula (IIa) or Formula (IIb):

trifluoroacetic acid, pentafluoroacetic acid, the o-, m- and p-trifluoromethylbenzoic acids can be mentioned.

As regards the carboxylic acid of Formula (III), those used preferably correspond to Formula (III) in which $R_2$ represents:

a linear or branched alkyl group, having 1 to 20 carbon atoms, preferably 1 to 12 carbon atoms, a cycloalkyl group having 3 to 8 carbon atoms, preferably a cyclopentyl or cyclohexyl group, an aryl group having 6 to 12 carbon atoms, preferably a phenyl or naphthyl group, an alkylaryl group having 7 to 12 carbon atoms, preferably a benzyl group.

As examples of carboxylic acids of Formula (IIb), acetic acid, acetic anhydride, propanoic acid, butanoic acid, pentanoic acid can be mentioned more particularly.

According to the process of the invention, the carboxylic acid ketonization reaction is carried out in the presence of a catalyst comprising at least one oxide of an element chosen from the rare earths, thorium, titanium and aluminum.

This is more particularly an oxide of a rare earth chosen from the lanthanides, yttrium, scandium and their mixtures, preferably the lanthanides such as lanthanium, cerium, praseodymium, neodymium, samarium, europium, gadolinium, terbium, dysprosium, holmium, erbium, thulium, ytterbium and lutetium.

Mixtures of thorium oxide and oxides of rare earths are preferably used. More particularly, the mixtures of thorium oxide and cerium oxide are chosen.

Mixtures comprising 20 to 40% of thorium oxide and 60 to 80% of rare earth oxide, preferably cerium are advantageously used.

Another type of catalytic element suitable for the implementation of the process of the invention is aluminum.

All the commercial aluminas can be used, but use of gamma alumina is preferred.

An alumina having a specific surface of at least 100 m²/g is advantageously used, preferably between 150 and 350 m²/gm, and more preferably between 200 and 280 m²/g.

Its porous volume most often varies between 0.2 and 1.0 cm³/g, preferably between 0.4 and 0.9 cm³/g.

The porous volume, like the specific surface, is measured according to the BRUNEAU-EMMETT-TELLER method, described in the periodical "The Journal of American Society 60,309 (1938)".

Generally, the alumina is used in the form of extrudates having a diameter of 0.5 to 5 mm, preferably 1 to 3 mm and a length of 2 to 100 mm, preferably 5 to 10 mm. It is also possible for it to be in the form of beads, pellets or granules.

The active ingredient is provided either directly in the form of oxide or obtained after calcination of a support impregnated using a solution providing the above-mentioned elements in the form of hydroxide, mineral or organic, single or double salt.

It is possible to use a hydroxide, preferably a mineral salt, nitrate, sulphate, oxysulphate, halogenide, oxyhalogenide, silicate, carbonate, oxalate, or a preferred organic salt, acetylacetonate; alcoholate, and yet more preferably methylate or ethylate; $C_1$–$C_6$ carboxylate such as acetate or also carboxylates derived from $C_8$–$C_{22}$ fatty acids and in particular stearate, palmitate, myristate and laurate.

The active ingredient is advantageously used in oxide form.

The nature of the support can be variable. Therefore, in particular the active carbons, silica gels, silica-alumina mixtures, alumina, clays (and more particularly, kaolin, talc or montmorillonite), bauxite, magnesia, and diatomaceous earth can be suitable for the present invention.

In the catalyst, the content of active phase represents 5 to 100% of the weight of the catalyst.

The catalysts can be presented in different forms in the process of the invention: powder, moulded products such as granules (for example extrudates or beads), pellets, which are obtained by extrusion, moulding, compacting or any other type of known process.

In order to prepare the supported catalyst so that it can be used for implementation of the process of the present invention, it is possible to resort to standard techniques, known per se, for preparation of supported metal catalysts. Reference can be made, in particular, for the preparation of the different catalysts, to the work: [J. F. LEPAGE "Catalyse de contact", conception, préparation et mise en oeuvre des catalyseurs industriels ["Contact catalysis", design, preparation and use of industrial catalysts], Edition Technip (1978)].

A known method for the preparation of metal oxides fixed on an inert support consists of dissolving in water a salt of the chosen metal, and pouring the solution obtained onto particles of the activated inert support. The mixture is then calcined between 400° and 600° C. in order to ensure the conversion of the metal salt to metal oxide fixed on the inert support.

According to the process of the invention, the ketonization reaction is carried out in the gaseous phase, by bringing the carboxylic acid (II) into contact with the carboxylic acid (III), in the presence of a catalyst as defined.

Generally, the quantity of the carboxylic acids used is such that the ratio between the number of moles of carboxylic acid (III) and the number of moles of carboxylic acid (II) varies between 1 and 20, preferably between 3 and 8.

According to the invention, the process is carried out in the gaseous phase. By this expression is meant that the different reagents are vaporized under reaction conditions, but the process does not exclude the presence of an optional liquid phase resulting either from the physical properties of the reagents, or from a use under pressure or the utilization of an organic solvent.

The vector gas is optional and is generally a gas or mixture of gases which are non-reactive under the reaction conditions. Gases such as nitrogen, air, argon or helium can be used. Advantageously, the volume ratio between the vector gas and the carboxylic acid (II) varies between 0 and 10, preferably between 0.1 and 2.0.

The temperature of the ketonization reaction is generally between 200° C. and 500° C., preferably between 250° C. and 450° C., and yet more preferably between 280° C. and 300° C.

The reaction pressure is preferably atmospheric pressure, but it is also possible to carry out the process under reduced pressure, which can go down to 100 mm of mercury when the starting reagents are not volatile.

According to the process of the invention, the starting reagents, i.e. the carboxylic acids, are vaporized. They are brought into contact with the catalyst, preferably carried along by a vector gas.

The WHSV (weight hourly space velocity) is between 0.05 and 1.5 $h^{-1}$, preferably between 0.1 and 0.8 $h^{-1}$.

In practice, the reaction is easily carried out continuously by passing the gaseous flux through a tubular reactor containing the catalyst.

First, the catalytic bed is prepared, which is constituted by the catalytic active phase, optionally deposited on a support (for example sintered glass), which allows the circulation of the gases without elution of the catalyst. Then, the reagents are introduced and several variants are possible.

It is possible to vaporize each of the reagents (II) and (III), in different chambers, then to carry out the mixing in a mixing chamber and to introduce the resultant gaseous flux onto the catalyst. The vector gas can be introduced in parallel with said gaseous flux or at the level of the mixing chamber.

Another variant consists of preparing a solution comprising the reagents (II) and (III), then vaporizing said mixture and introducing it onto the catalyst, in parallel with the vector gas.

Another practical embodiment of the invention consists of melting one of the carboxylic acids by heating it to its melting temperature and passing it over a gaseous flux comprising the other carboxylic acid. This flux is saturated with the first carboxylic acid and it is then brought into contact with the catalyst.

Another embodiment of the invention uses an organic solvent which is inert under the reaction conditions and which is chosen so that it solubilizes the carboxylic acid (II) and the carboxylic acid (III) used.

According to the invention, an aprotic solvent is preferably used, having a boiling point above 60°, preferably between 60° C. and 300° C.

As aprotic solvents capable of being used in the process of the invention, the aliphatic or aromatic hydrocarbons, such as hexane, heptane, cyclohexane, benzene, toluene, the xylenes can be mentioned.

Several solvents can also be used.

The quantity of carboxylic acid (II) introduced into the solvent is generally such that the solvent/carboxylic acid (II) molar ratio is between 0 and 20, and, preferably, between 0 and 5.

An organic solution is therefore prepared, comprising the carboxylic acid (II), the carboxylic acid (III), then said mixture is vaporized and introduced onto the catalyst, in parallel with the vector gas.

At the end of the reaction, the mixture of the gases is condensed and the non-reacted reagents and the products obtained are separated, by distillation or fractional crystallization. It is also possible to separate these by fractional condensation. In the more particular case of trifluoroacetone, the latter is recovered in hydrate form, by trapping the gaseous flux in water.

The process of the invention can make it possible to preferably obtain a ketone corresponding to Formula (I) of perfluorinated type.

The process of the invention is perfectly well adapted to the preparation of trifluoroacetone.

The process can be implemented continuously.

The preferred embodiment of the invention involves use of an alumina-type catalyst. The catalyst of the invention can easily be regenerated by air treatment between 450° C. and 500° C. It is maintained under air until no more carbon dioxide is released.

The regeneration of the catalyst can be carried out separately or in situ.

The regenerated catalyst retains all its catalytic performance.

The examples which follow illustrate the invention, without however limiting it.

EXAMPLES

In the different examples which follow, the abbreviations CR, RY have the following meanings:

$$\text{Conversion rate} = CR = \frac{\text{number of moles of carboxylic acid} * \text{converted}}{\text{number of moles of carboxylic acid} * \text{introduced}} \text{in \%}$$

$$\text{Real yield} = RY = \frac{\text{number of moles of ketones formed}}{\text{number of moles of carboxylic acid} * \text{introduced}} \text{in \%}$$

\* : the acid concerned is the acid introduced by default.

Example 1

Into a glass reactor, 25 mm in diameter, the following are introduced successively:
- 5 ml of quartz, with granulometry of 300–600 μm
- 3 ml of $CeO_2/ThO_2$ (62/38) catalyst
- 5 ml of quartz.

The reactor is placed in an electric oven and a collecting tube is connected to the base of the reactor.

A stream of nitrogen is passed through at 3 l/h, and the oven is heated to 350° C. over one hour.

Once the activation is completed, the temperature is taken to 280° C. and 3.2 ml/h of a trifluoroacetic acid mixture in acetic acid at 10% p/p is injected using a syringe driver.

The effluent gases are trapped in a trap containing water in order to form trifluoroacetone hydrate.

After 3 hours of reaction, the following results are obtained by chromatography in the gaseous phase:

| | |
|---|---|
| CR trifluoroacetic acid: | 83% |
| RY trifluoroacetone: | 42% |

Example 2

Example 1 is reproduced with the difference that 1 ml of $CeO_2/ThO_2$ catalyst is introduced.

The following results are obtained:

| | |
|---|---|
| CR trifluoroacetic acid: | 23% |
| RY trifluoroacetone: | 4% |

Example 3

Example 1 is reproduced with the 3 ml of $CeO_2/ThO_2$ (72/28) catalyst.

The following results are obtained:

| | |
|---|---|
| CR trifluoroacetic acid: | 78% |
| RY trifluoroacetone: | 35% |

Example 4

Into a 30 ml glass reactor, 20 ml of gamma alumina is introduced, with a specific surface=280 $m^2/g$ and total porous volume of 0.8 $cm^3/g$ in the form of extrudates (1.2 mm in diameter, 5 to 10 mm in length).

The reactor is heated to 280° C. with a nitrogen flow rate of 2 litres per hour and maintained for 1 hour under these conditions.

A mixture of trifluoroacetic acid in acetic anhydride at 10% P/P is injected at a flow rate of 11 ml/h.

The reaction gases are then partially condensed in a flask maintained at 25° C. in order to recover the reagents which have not reacted, then in a trap containing water in order to recover the trifluoroacetone formed in hydrate form.

After 5 hours of reaction, NMR analysis gives us the following results:

| | |
|---|---|
| CR trifluoroacetic acid: | 83% |
| RY trifluoroacetone: | 70% |

Example 5

The previous example is repeated, but the reaction is carried out at 230° C.

Under these conditions, the results obtained are as follows:

| | |
|---|---|
| CR trifluoroacetic acid: | 47% |
| RY trifluoroacetone: | 31% |

Example 6

The preceding Example 4 is repeated, but 6 ml/h of a 20% P/P mixture of trifluoroacetic acid in acetic anhydride are injected.

Under these conditions, the results obtained are as follows:

| | |
|---|---|
| CR trifluoroacetic acid: | 79% |
| RY trifluoroacetone: | 64% |

Example 7

The preceding Example 4 is repeated, but an alpha alumina is used.

Under these conditions, the results obtained are as follows:

| | |
|---|---|
| CR trifluoroacetic acid: | 24% |
| RY trifluoroacetone: | 5% |

Example 8

Recycling of the Catalyst.

After deactivation of the catalyst of Example 4, this is calcined under a stream of air at 3 l/h for 15 hours at 500° C.

The temperature is then taken to 280° C. and the injections are recommenced under the same conditions.

The following results are obtained:

| CR trifluoroacetic acid: | 81% |
| RY trifluoroacetone: | 71% |

The catalyst can be recycled without significant loss of activity.

What is claimed is:

1. A process for the preparation of a fluorinated ketone of general formula:

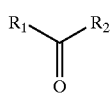    (I)

wherein:
$R_1$ and $R_2$, which are identical or different, represent a hydrocarbon group containing 1 to 40 carbon atoms, with the further proviso that:
at least one of the $R_1$ and $R_2$ groups does not comprise hydrogen atoms on the carbon atom at position α with respect to the carbonyl group, and
at least one of the $R_1$ and $R_2$ groups comprises one or more fluorine atoms,
said process comprising the steps of:
(a) reacting in gaseous phase a carboxylic acid of Formula (II):

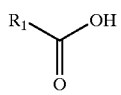    (II)

wherein $R_1$ is as defined above, and a carboxylic acid of formula (III):

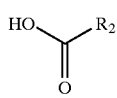    (III)

wherein $R_2$ is as defined above,
in the presence of a catalyst comprising at least one oxide of a metallic element which is a rare earth, thorium, titanium or aluminum; and
(b) recovering the ketone of general formula (I) from step (a).

2. The process according to claim 1, wherein the metallic element is deposited on a support.

3. The process according to claim 2, wherein the support is silica, alumina, a silica-alumina mixture, clays, bauxite, magnesia, or diatomaceous earth.

4. The process according to claim 1, wherein the catalyst is a mixture of thorium oxide and rare earth oxide.

5. The process according to claim 4, wherein the rare earth oxide is cerium oxide.

6. The process according to claim 4, the catalyst is a mixture comprising 20 to 40% of thorium oxide and 60 to 80% of rare earth oxide.

7. The process according to claim 6, wherein the rare earth oxide is cerium oxide.

8. The process according to claim 1, wherein the catalyst is alumina.

9. The process according to claim 8, wherein the alumina is gamma alumina.

10. The process according to claim 1, wherein in formula (II) or (III), $R_1$ and $R_2$ represent:
a linear or branched, saturated or unsaturated acyclic aliphatic group;
a monocyclic or polycyclic, saturated, unsaturated or aromatic carbocyclic or heterocyclic group; or a sequence of the above-mentioned groups.

11. The process according to claim 1, wherein in formula (II) or (III), $R_1$ and $R_2$ represent:
a linear or branched acyclic aliphatic group,
an acyclic aliphatic group, carrying a cyclic substituent, optionally substituted, which is bonded to the ring by a valency bond, a heteroatom or a functional group, a saturated or unsaturated carbocyclic group having 5 or 6 carbon atoms in the ring; a
saturated or unsaturated heterocyclic group, containing 5 or 6 carbon atoms in the ring, including 1 or 2 heteroatoms which are nitrogen, sulphur or oxygen atoms; a monocyclic, aromatic carbocyclic or heterocyclic group, or polycyclic, condensed or non-condensed.

12. The process according to claim 1, wherein $R_1$ and $R_2$ represent:
a benzene ring, phenyl, pyridyl, or naphthyl.

13. The process according to claim 1, wherein $R_1$ and $R_2$ represent a linear or branched alkyl group, having 1 to 12 carbon atoms.

14. The process according to claim 1, wherein the carboxylic acid of Formula (II) comprises a tertiary carbon atom situated at position α with respect to the carbonyl group, and which is represented by the formula $(R_3)(R_4)(R_5)$C—, wherein $R_3$, $R_4$, $R_5$ represent a halogen atom; a linear or branched alkyl group having 1 to 6 carbon atoms, the $R_3$, $R_4$ and $R_5$ groups optionally forming a ring.

15. The process according to claim 14, wherein the $R_3$, $R_4$ and $R_5$ groups represent a fluorine atom or form a phenyl group.

16. The process according to claim 1, wherein the carboxylic acid of Formula (II) is a fluorinated aliphatic carboxylic acid corresponding to formula (IIa):

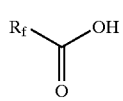    (IIa)

wherein:
$R_f$ represents a perfluorinated chain of formula:

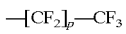

wherein p represents a number from 0 to 10.

17. The process according to claim 16, wherein the carboxylic acid corresponds to Formula (IIa) wherein $R_f$ represents the groups:

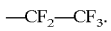

18. The process according to claim 1, wherein the carboxylic acid of Formula (II) is a fluorinated aromatic carboxylic acid corresponding to Formula (IIb):

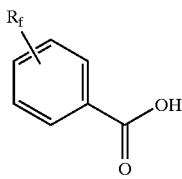
(IIb)

wherein $R_f$ represents a perfluorinated chain of formula:

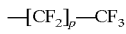

wherein p represents a number from 0 to 10.

19. The process according to claim 18, wherein $R_f$ is a trifluoromethyl group.

20. The process according to claim 1, wherein the carboxylic acid of Formula (IIa) or (IIb) is trifluoroacetic acid, pentafluoroacetic acid, o-trifluoromethylbenzoic acid, m-trifluoromethylbenzoic acid or p-trifluoromethylbenzoic acid.

21. The process according to claim 1, wherein the carboxylic acid of Formula (III) is a carboxylic acid corresponding to Formula (III) wherein $R_2$ represents:

a linear or branched alkyl group, having 1 to 20 carbon atoms, a cycloalkyl group having 3 to 8 carbon atoms, an aryl group having 6 to 12 carbon atoms, or an alkylaryl group having 7 to 12 carbon atoms.

22. The process according to claim 21, wherein $R_2$ represents:

a linear or branched alkyl group, having 1 to 12 carbon atoms, a cyclopentyl, cyclohexyl group, a phenyl, naphthyl group, or a benzyl group.

23. The process according to claim 1, wherein the carboxylic acid of Formula (III) is acetic acid, acetic anhydride, propanoic acid, butanoic acid, or pentanoic acid.

24. The process according to claim 1, wherein the carboxylic acid of Formula (II) is trifluoroacetic acid and the acid of Formula (III) is acetic acid.

25. The process according to claim 1, wherein the carboxylic acid is added with a ratio between the number of moles of carboxylic acid (III) and the number of moles of carboxylic acid (II) varying between 1 and 20.

26. The process according to claim 25, wherein the ratio varies between 3 and 8.

27. The process according to claim 1, wherein the WHSV (weight hourly space velocity) is between 0.05 and $1.5h^{-1}$, preferably between 0.1 and 0.8 $h^{-1}$.

28. The process according to claim 1, wherein the step a) further comprising the use of a non-reactive vector gas or a mixture of gases.

29. The process according to claim 28, wherein said vector gas is nitrogen, air, argon or helium.

30. The process according to claim 28, wherein said vector gas is used in a volume ratio between the vector gas and the carboxylic acid (II) varying between 0.1 and 10.

31. The process according to claim 1, wherein the step a) further comprising the use of an organic aprotic solvent which solubilizes the carboxylic acids.

32. The process according to claim 1, wherein the reaction of step a) is a ketonization reaction carried out at a temperature of between 200° C. and 500° C.

33. The process according to claim 32, wherein the temperature is between 280° C. and 300° C.

34. The process according to claim 1, wherein the reaction of step a) is carried out at atmospheric pressure.

35. The process according to claim 1, wherein the step a) further comprising vaporizing the carboxylic acids, and, then, bringing them into contact with the catalyst.

36. The process according to claim 35, wherein the acids are brought into contact with the catalyst by a vector gas.

* * * * *